(12) United States Patent
Welch et al.

(10) Patent No.: US 10,130,379 B2
(45) Date of Patent: Nov. 20, 2018

(54) THROMBUS EXTRACTION CATHETER

(71) Applicant: NorMedix, Inc., Eden Prairie, MN (US)

(72) Inventors: Jeffrey M. Welch, Maple Grove, MN (US); Karl V. Ganske, Hopkins, MN (US); Gregg Stuart Sutton, Plymouth, MN (US)

(73) Assignee: NorMedix, Inc., Eden Prairie, MN (US)

( * ) Notice: Subject to any disclaimer, the term of this patent is extended or adjusted under 35 U.S.C. 154(b) by 248 days.

(21) Appl. No.: 14/786,851

(22) PCT Filed: Apr. 23, 2014

(86) PCT No.: PCT/US2014/035142
§ 371 (c)(1),
(2) Date: Apr. 14, 2016

(87) PCT Pub. No.: WO2014/176332
PCT Pub. Date: Oct. 30, 2014

(65) Prior Publication Data
US 2016/0106446 A1    Apr. 21, 2016

Related U.S. Application Data

(60) Provisional application No. 61/815,160, filed on Apr. 23, 2013.

(51) Int. Cl.
*A61B 17/22* (2006.01)
*A61L 29/02* (2006.01)
(Continued)

(52) U.S. Cl.
CPC .............. *A61B 17/22* (2013.01); *A61L 29/02* (2013.01); *A61L 29/041* (2013.01); *A61L 29/06* (2013.01);
(Continued)

(58) Field of Classification Search
CPC ......... A61B 17/22; A61B 2017/22079; A61M 25/0043; A61M 25/005; A61M 25/0052;
(Continued)

(56) References Cited

U.S. PATENT DOCUMENTS 6,152,909 A * 11/2000 Bagaoisan ............. A61B 17/22
                                                    604/173
7,608,063 B2   10/2009 Le et al.
(Continued)

FOREIGN PATENT DOCUMENTS

EP    1639951 A1    3/2006
EP    2988684       3/2016
(Continued)

OTHER PUBLICATIONS

"European Application Serial No. 14789021.4, Communication pursuant to Rules 161(2) and 162 EPC dated Dec. 11, 2015", 2 pgs.
(Continued)

*Primary Examiner* — Thomas McEvoy
(74) *Attorney, Agent, or Firm* — Schwegman Lundberg & Woessner, P.A.

(57) ABSTRACT

Embodiments of the invention include a multi-lumen catheter for extracting or aspirating a blood clot or thrombus from arterial or venous sites. Other embodiments are also included herein.

31 Claims, 1 Drawing Sheet

(51) Int. Cl.
  *A61L 29/04* (2006.01)
  *A61L 29/06* (2006.01)
  *A61M 25/00* (2006.01)
  *A61L 29/08* (2006.01)
  *A61L 29/10* (2006.01)
  *A61L 29/18* (2006.01)
  *A61M 25/01* (2006.01)
  *A61B 90/00* (2016.01)

(52) U.S. Cl.
  CPC ......... *A61L 29/085* (2013.01); *A61L 29/106* (2013.01); *A61L 29/18* (2013.01); *A61M 25/005* (2013.01); *A61B 2017/22039* (2013.01); *A61B 2017/22042* (2013.01); *A61B 2017/22079* (2013.01); *A61B 2090/3966* (2016.02); *A61M 2025/0046* (2013.01); *A61M 2025/0059* (2013.01); *A61M 2025/0183* (2013.01)

(58) Field of Classification Search
  CPC .......... A61M 25/0067; A61M 25/0068; A61M 25/0069
  See application file for complete search history.

(56) References Cited

U.S. PATENT DOCUMENTS

| | | |
|---|---|---|
| 2006/0276774 A1 | 12/2006 | Mori |
| 2007/0106211 A1 | 5/2007 | Provost-tine et al. |
| 2009/0270800 A1* | 10/2009 | Spurchise ......... A61M 25/0074 604/95.04 |
| 2012/0016344 A1* | 1/2012 | Kusakabe ......... A61M 25/0021 604/528 |

FOREIGN PATENT DOCUMENTS

| | | |
|---|---|---|
| JP | 2010057831 A | 3/2010 |
| WO | WO-2014176332 | 10/2014 |

OTHER PUBLICATIONS

"European Application Serial No. 14789021.4, Extended European Search Report dated Nov. 23, 2016", 8 pgs.

"European Application Serial No. 14789021.4, Response filed Oct. 4, 2017 to Extended European Search Report dated Nov. 23, 2016", 9 pgs.

* cited by examiner

THROMBUS EXTRACTION CATHETER

CLAIM OF PRIORITY

This application is a U.S. National Stage Filing under 35 U.S.C. § 371 of International Patent Application Serial No. PCT/US/2014/035142, filed Apr. 23, 2014, and published on Oct. 30, 2014 as WO 2014/176332, which claims priority to U.S. Provisional Patent Application No. 61/815,160, filed Apr. 23, 2013, the contents of which are herein incorporated by reference in their entirety.

FIELD OF THE INVENTION

The present invention relates to multi-lumen catheter for extracting or aspirating blood clot or thrombus from arterial or veinous sites.

BACKGROUND

In coronary and peripheral interventions requiring revascularization, many times a clot has formed proximal to the atherosclerotic lesion. Extraction of the clot prior to angioplasty or stenting can be preferred to reduce the possibility of distal emboli.

Systems available to physicians, including distal protection filters and mechanical clot maceration devices, are subject to limitations including difficult placement and manipulation, time to prepare and deliver devices, required occlusion of blood flow, and other complications such as arterial spasm and dissection. These devices in general are over-complicated and bring additional risks to the procedure. In addition, problems associated with the currently available thrombus extraction catheters include; kinking, buckling, stretching and ovaling. These problems all reduce the ability to quickly extract thrombus or navigate to the treatment site. The device of this invention solves these limitations by providing a means to quickly and directly remove the thrombus burden present in arterial and veinous interventions while maintaining the device mechanical integrity.

SUMMARY OF THE INVENTION

Embodiments of the invention include a two lumen catheter for use in arterial or veinous interventional procedures for extracting thrombus or a clot. The catheter can comprise a first main lumen for sucking or aspirating the blood clot. The first main lumen extends from the distal tip to the proximal end. The distal portion of the first main lumen can comprise metaland can be constructed from a swaged, tightly spaced metal coil, such that the individual coil wire cross-section are substantially rectangular in shape. A proximal portion of the first lumen can comprise metal tubing and be attached to the distal portion. The proximal portion can terminate at its proximal end with a luer adapter.

A second guidewire passing lumen extending from the distal tip and exiting or terminating at a point proximal of the distal tip at a distance of lcm to 50 cm. The guidewire lumen can be attached adjacent to the outside wall of the first, main lumen.

A distal tip structure attached to the distal portion of the first main lumen is angled at its distal end 30-60 degrees from the central axis of the lumen. The distal tip can be attached by metal fusion to the distal coil portion. The distal tip can be externally coated with gold plating for enhanced radiopactiy.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

DETAILED DESCRIPTION OF THE INVENTION

Figure 1:
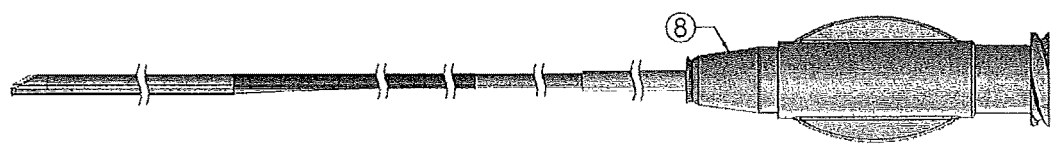
FIG. 1 is a perspective view of the device.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The catheter device of this invention is a two-lumen catheter that is manipulated or navigated to the arterial or veinous site where thrombus is present.

One of the lumens in the catheter of this invention is for railing over a guidewire (for example an 0.014") that is typically used to access the arterial or veinous site or branch. The catheter can be railed over a guidewire and inserted within an interventional guide catheter. The second lumen of the catheter is used mainly for sucking or aspirating the thrombus/clot. This is accomplished by attaching a large capacity syringe to the proximal second lumen luer adapter and pulling a vacuum on the syringe so as to cause suction at the distal tip of the catheter. In one embodiment, the distal tip of the catheter of this invention has a guard strut protecting the distal tip opening from being sucked against the arterial or veinous wall. In another embodiment, the distal tip is slightly angled to provide maximum cross-sectional opening at the tip.

The device of this invention can solve the problems associated with current guide catheter technology by providing a novel design, construction and materials. The thrombus catheter design of this invention can comprise a composite built tube that is fabricated using a specially wound metal inner layer and jacketed with very thin layers of polymer inside and out. The metallic inner layer can be made using a multi-filar, such as 6-20 filars, helically wound wire structure. In an embodiment, the multi-filar helically wound wire structure can include stainless steel. In an embodiment of this invention, the helical structure can be swaged such that each individual wire strand in partially rectangular in cross-section and can result in a tightly spaced, close fitting, or intimate wire matrix. In an embodiment, the catheter can be made using a non-swaged, round, circular, oval, elliptical, square or rectangular wire. In an embodiment, the multi-filar structure wires can be coated with PTFE, such as prior to forming the multi-filar configuration. In an embodiment, the typical wall thickness of the inner metal structure can be at least 1.5 thousandths of an inch think and no more than 10 thousandths of an inch thick. In an embodiment, the mulit-filar layer can have welded terminations.

The helically wound metal structure can provide a significant improvement in mechanical integrity of the catheter tube compared to current catheters with respect to kinking, buckling, flexibility, radial strength, and maintaining circularity of the catheter lumen cross-section. This marked improvement can be achieved by the significant increase in the amount of metal in the catheter. For instance, current interventional catheters that are composite built or wire braid reinforced have total cross-sectional metallic component in the range of 5-10%. The catheter can have a total cross-sectional metallic component of 35-65%. The transmission of mechanical energy through this significantly higher modulus composite can result in significantly higher performance.

The thrombus extraction catheter can also comprise outer and inner polymer 25 layers or jacket made of various polymers, such as nylon, PTFE, Pebax®, Polyurethane, a hydrophilic polymer, or other similar polymers. The inner polymer layer can be disposed on the inside surface of the catheter, such as the surface defining a lumen. The outer polymer layer can be disposed on the outside surface of the catheter, such as the surface that is external to a lumen, in an embodiment, the outer or inner 30 polymer layers can include a composite of two or more polymers, such as a composite of PTFE and Pebax®. In an embodiment, the outer and inner polymer layers can include different materials, such as the inner layer including PTFE and the outer layer including Pebax®. In an embodiment, the outer or inner polymer layer can include two or more layers, such as the outer polymer layer including two layer of Pebax®. The polymer layers can be attached to the metal structure, such as by thermal polymer heat-shrinking or reflow. The polymer layers can be heat shrinkable, such as to allow it to be formed tightly only the helical multi-filar structure. The resultant wall thickness of the polymer layers can be between 1.0-3.0 thousandths of an inch for each layer.

The construction and performance of the thrombus extraction catheter makes it ideally suited for interventional cases where significant vascular tortuosity is encountered such as using a radial artery access or using a femoral approach on an obese patient.

The guide catheter can also comprise an angled, soft (low durometer) polymer distal tip, a radiopaque distal marker band, and a proximal luer adapter. The thrombus extraction catheter of this invention could be made for instance in sizes from 3 F-8 F and in lengths of 80-175 cm.

In reference to the Figures, FIG. 1 shows a perspective view of a catheter. The catheter can include a luer adapter 8. In an embodiment, the luer adapter 8 can be coupled or attached to the proximal end of the catheter. The luer adapter 8 can be configured to couple or attach a suction device to the catheter. The outer diameter of the catheter, such as the outer diameter of the main tubular shaft can be 0.039-0.105 inches.

Figure 2:
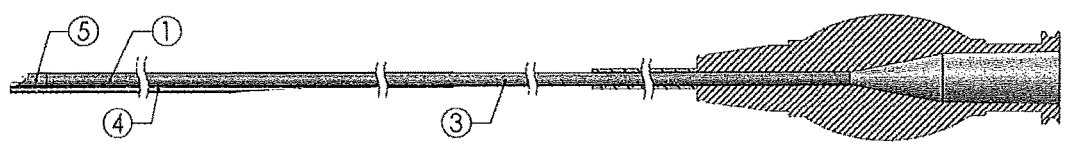
FIG. 2 is a section view of the device showing its parts

FIG. 2 shows a cross-section of the catheter. The catheter can include a first main lumen 1, a second lumen 4, a distal tip structure 5, and a proximal portion 3. The second lumen 4 can be configured for a guidewire to pass through the lumen. The distal tip structure 5 can be coupled to the distal portion of the first main lumen, such as with metal fusion. The distal tip structure 5 can be angled at its distal end, such as from 30-60 degrees from the central axis of the lumen.

Figure 3:
FIG. 3 is a perspective view of the device with further distal tip embodiment

FIG. 3 shows a perspective view of a catheter with an alternative embodiment of the distal tip potion 7. The distal tip portion 7 can include metal, such as being constructed primarily of metal. The distal tip portion 7 can include a strut attached to the outside wall of the first main lumen and extending distally and attached at a second point to the second lumen at a point distal to the termination of the first lumen, such as to provide a guard inhibiting suction of the artery or vein wall against the first lumen opening. In an embodiment, the 0.5-2.0 mm of the distal tip can be coated with gold.

Figure 4:
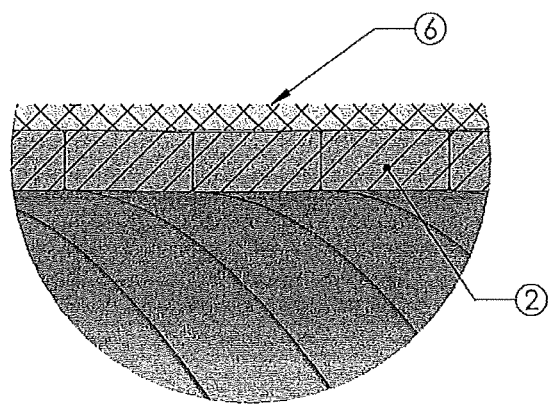
FIG. 4 is a section view of a portion of the wall of the first lumen While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

FIG. 4 shows a cross-section of a portion of the wall of the first lumen. The first lumen can include a polymeric layer 6. The first lumen can include a multi-filar coil structure 2. The internal surface of the first lumen can be coated with a silicone friction reducing polymer.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A two lumen catheter for use in arterial or veinous interventional procedures for extracting thrombus or clot comprising:
   a first main lumen configured for sucking or aspirating a blood clot, the first main lumen extending from a distal end to a proximal end, the first lumen comprising metal with a metal internal surface where a distal portion of the first lumen is constructed from a swaged, multi-filar coil structure, such that the individual coil wire cross-sections are substantially rectangular in shape, a proximal portion of the first lumen attached to the distal portion and being made of substantially metal tubing, the proximal portion of the first lumen being metallically fused to the distal portion, the proximal portion being terminated at its proximal end with a luer adapter;

a second lumen, configured for a guidewire to pass through, extending from the distal tip and exiting or terminating at a point proximal of the distal tip at a distance of 1-50 cm, the second lumen being attached adjacent to an outside wall of the first main lumen; and a distal tip attached to the distal portion of the first main lumen that is substantially constructed of metal and angled at its distal end in an amount of 30-60 degrees from a central axis of the first main lumen, the distal tip attached by metal fusion to the distal portion, the distal tip being coated with a gold plating for enhanced radiopacity.

2. The two lumen catheter of claim 1, wherein the distal tip is made substantially of metal and has a strut attached to the outside wall of the first main lumen and extending distally and attached at a second point to the second lumen at a point distal to the termination of the first lumen so as to provide a guard inhibiting suction of the artery or vein wall against the first lumen opening.

3. The two lumen catheter of claim 1, wherein entire external and internal surfaces of the device are jacketed or coated with a polymeric layer.

4. The two lumen catheter of claim 3, wherein the external polymeric layer is made of PTFE.

5. The two lumen catheter of claim 3, wherein the external polymeric layer is made of nylon.

6. The two lumen catheter of claim 3, wherein the external polymeric layer is coated with a hydrophilic polymer.

7. The two lumen catheter of claim 3, wherein the internal polymeric layer is made of PTFE.

8. The two lumen catheter of claim 3, wherein the internal polymeric layer is made of a PTFE/Pebax® composite layer.

9. The two lumen catheter of claim 3, wherein the internal polymeric layer is made of nylon.

10. The two lumen catheter of claim 3, wherein the internal polymeric layer is coated with a hydrophilic polymer.

11. The two lumen catheter of claim 3, wherein the external polymeric layer is made of Pebax®.

12. The two lumen catheter of claim 3, wherein the external polymeric layer is made of two layers of Pebax®.

13. The two lumen catheter of claim 3, wherein the external polymeric layer is heat shrinkable to allow it to be formed tightly onto the helical multi-filar coil structure.

14. The two lumen catheter of claim 1, wherein the external surface of the distal portion of the device is coated with hydrophilic polymer.

15. The two lumen catheter of claim 1, wherein the internal surface of the first lumen is coated with a silicone friction reducing polymer.

16. The two lumen catheter of claim 1, wherein the distal portion of the first main lumen includes individual coil wire cross-sections that are elliptical in shape.

17. The two lumen catheter of claim 1, wherein the multi-filar coil structure includes stainless steel.

18. The two lumen catheter of claim 1, wherein the multi-filar coil structure includes 6-20 filars.

19. The two lumen catheter of claim 1, wherein the multi-filar coil structure is swaged and imparts a rectangular cross-section and intimate fitting contact between the individual coil wire cross-sections.

20. The two lumen catheter of claim 1, wherein an outer diameter of the first main lumen is between .039-0.105".

21. The two lumen catheter of claim 1, wherein the distal portion is made of a PTFE inner layer and Pebax® outer layer.

22. The two lumen catheter of claim 1, wherein the helical multi-filar coil structure has welded terminations.

23. The two lumen catheter of claim 1, wherein the helical multi-filar coil structure has a distal tip that has been coated with gold for 0.5-2 mm.

24. The two lumen catheter of claim 1, wherein the multi-filar coil structure wires each include a rectangular cross-section.

25. The two lumen catheter of claim 1, wherein the multi-filar coil structure wires each include a circular cross-section.

26. The two lumen catheter of claim 1, wherein the multi-filar coil structure wires each include an oval or elliptical cross-section.

27. The two lumen catheter of claim 1, wherein the multi-filar coil structure wires are coated with PTFE coating prior to forming into the multi-filar coil structure.

28. The two lumen catheter of claim 1, wherein the first lumen comprises at least 35 percent metal.

29. The two lumen catheter of claim 1, wherein the first lumen comprises 35-65 percent metal.

30. The two lun e catheter of claim 1, the distal portion is 10-50 cm in length.

31. The two lumen catheter of claim 1, proximal portion is 50-100 cm in length.

\* \* \* \* \*

UNITED STATES PATENT AND TRADEMARK OFFICE
CERTIFICATE OF CORRECTION

PATENT NO. : 10,130,379 B2  
APPLICATION NO. : 14/786851  
DATED : November 20, 2018  
INVENTOR(S) : Welch et al.

Page 1 of 1

It is certified that error appears in the above-identified patent and that said Letters Patent is hereby corrected as shown below:

In the Claims

In Column 6, Line 46, in Claim 30, delete "lun e" and insert --lumen-- therefor

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*